(12) United States Patent
Egan

(10) Patent No.: US 12,257,423 B2
(45) Date of Patent: Mar. 25, 2025

(54) PEN NEEDLE

(71) Applicant: Embecta Corp., Andover, MA (US)

(72) Inventor: Pearse Egan, Dublin (IE)

(73) Assignee: Embecta Corp., Andover, MA (US)

( * ) Notice: Subject to any disclaimer, the term of this patent is extended or adjusted under 35 U.S.C. 154(b) by 1128 days.

(21) Appl. No.: 17/252,165

(22) PCT Filed: Jun. 7, 2019

(86) PCT No.: PCT/US2019/036028
§ 371 (c)(1),
(2) Date: Dec. 14, 2020

(87) PCT Pub. No.: WO2019/245757
PCT Pub. Date: Dec. 26, 2019

(65) Prior Publication Data
US 2021/0283344 A1    Sep. 16, 2021

Related U.S. Application Data

(60) Provisional application No. 62/688,572, filed on Jun. 22, 2018.

(51) Int. Cl.
*A61M 5/50* (2006.01)
*A61M 5/32* (2006.01)
*A61M 5/34* (2006.01)

(52) U.S. Cl.
CPC ........ *A61M 5/5086* (2013.01); *A61M 5/3243* (2013.01); *A61M 5/3293* (2013.01);
(Continued)

(58) Field of Classification Search
CPC ...... A61M 5/5086; A61M 5/00; A61M 5/158; A61M 5/162; A61M 5/1626;
(Continued)

(56) References Cited

U.S. PATENT DOCUMENTS 5,188,599 A * 2/1993 Botich ............... A61B 5/15003
604/110
5,338,310 A   8/1994 Lewandowski
(Continued)

FOREIGN PATENT DOCUMENTS

CN        101454032        6/2009
CN        110624161 A     12/2019
(Continued)

OTHER PUBLICATIONS

International Search Report dated Oct. 29, 2019, which issued in the corresponding PCT Patent Application PCT/US2019/036028.

*Primary Examiner* — Kevin C Sirmons
*Assistant Examiner* — Alexandra Lalonde
(74) *Attorney, Agent, or Firm* — Greenberg Traurig, LLP; David J. Dykeman; Roman Fayerberg

(57) ABSTRACT

A pen needle includes a hub supporting a needle and a distal needle shield that can retract to expose the needle and return to an extended position to cover the needle. A proximal needle shield moves to an extended position to cover a proximal end of the needle. A spring extends between the distal and proximal needle shields to bias the distal and proximal needle shields to their respective extended positions. A locking member on the distal needle shield cooperates with the hub to lock the proximal and distal needle shields in their respective extended positions. An indicator in the hub couples to the distal needle shield when the distal needle shield is moved to a retracted position. The indicator moves with the distal needle shield to the extended position of the distal needle shield where the indicator indicates that the pen needle is no longer usable.

20 Claims, 12 Drawing Sheets

(52) U.S. Cl.
CPC .............. *A61M 5/346* (2013.01); *A61M 5/50* (2013.01); *A61M 2005/3254* (2013.01)

(58) Field of Classification Search
CPC ............ A61M 5/31566; A61M 5/3157; A61M 5/31571; A61M 5/32; A61M 5/3202; A61M 5/3205; A61M 5/321; A61M 5/3213; A61M 5/3243; A61M 5/3245; A61M 5/3257; A61M 5/326; A61M 5/3269; A61M 5/3271; A61M 5/3272; A61M 5/3275; A61M 5/3287; A61M 5/343; A61M 5/345; A61M 5/346; A61M 5/347; A61M 5/50; A61M 5/3293; A61M 2005/1585; A61M 2005/1588; A61M 2005/3107; A61M 2005/312; A61M 2005/3206; A61M 2005/3217; A61M 2005/3223; A61M 2005/3247; A61M 2005/3252; A61M 2005/3254; A61M 2005/3261; A61M 2005/3267; A61M 2005/3268; A61M 2005/3258; A61M 25/0612; A61M 25/0618; A61M 25/0625; A61M 25/0631; A61M 2205/58; A61M 2205/583; A61M 2205/584
See application file for complete search history.

(56) References Cited

U.S. PATENT DOCUMENTS

| | | |
|---|---|---|
| 7,645,264 B2 | 1/2010 | Marsh et al. |
| 8,057,444 B2 | 11/2011 | Hartmann et al. |
| 9,774,844 B2 | 9/2017 | Yang et al. |
| 2009/0069755 A1 | 3/2009 | Horvath |
| 2009/0254042 A1 | 10/2009 | Gratwohl et al. |
| 2010/0234811 A1 | 9/2010 | Schubert et al. |
| 2011/0160675 A1* | 6/2011 | Ruan ................... A61M 5/3272 604/198 |
| 2012/0022460 A1 | 1/2012 | Horvath et al. |
| 2013/0046246 A1 | 2/2013 | Cross et al. |
| 2013/0172818 A1 | 7/2013 | Schraga |
| 2015/0157808 A1* | 6/2015 | Srinivasan .......... A61M 5/3293 604/198 |
| 2015/0328412 A1 | 11/2015 | Bates et al. |
| 2016/0228654 A1 | 8/2016 | Rozwadowski et al. |
| 2017/0304556 A1 | 10/2017 | Carpenter et al. |
| 2018/0339115 A1* | 11/2018 | Limaye ............... A61M 5/3202 |

FOREIGN PATENT DOCUMENTS

| | | |
|---|---|---|
| CN | 211561409 U | 9/2020 |
| GB | 2 537 441 A1 | 10/2016 |
| JP | 2010512884 A | 4/2010 |
| JP | 2015134156 A | 7/2015 |
| JP | 2015186728 A | 10/2015 |
| WO | 01/76665 A1 | 10/2001 |
| WO | 2001076665 A1 | 10/2001 |
| WO | 2017147817 A1 | 9/2017 |

* cited by examiner

PEN NEEDLE

This application is a national stage application, filed under 35 U.S.C. § 371, of International Patent Application No. PCT/US2019/036028, filed on Jun. 7, 2019, which claims priority to U.S. Provisional Patent Application Ser. No. 62/688,572 filed on Jun. 22, 2018, which are hereby incorporated by reference in their entireties.

BACKGROUND

Field of the Disclosure

The disclosure is directed to a pen needle adapted for attachment to a medication delivery device, such as a medication delivery pen. The pen needle in one embodiment has a needle hub with a retractable needle shield where the needle shield can be retracted during use and extended after use to cover the needle attached to the hub. After use of the needle, the needle shield can be locked in the extended position to cover the end of the needle. The pen needle can include a distal needle shield for covering the patient end of the needle after use and a proximal needle shield for covering the non-patient proximal end of the needle after separation from the delivery device. A visual indicator can be provided that can be actuated when the distal needle shield covers the patient end of the needle.

Description of the Related Art

Pen needles are used to attach to a medication pen and are especially useful for delivering self-administered injectable medications such as insulin. In one known commercial device, a needle-bearing hub is provided inside a funnel-shaped outer cover, sometimes referred to as the "outer shield," or simply as the "cover." The cannula or needle is affixed in an axial bore of the hub with one end protruding from the distal or "patient side" of the hub for injecting the patient and the other end of the needle is recessed in a cavity on the proximal or "non-patient" side of the hub, and is adapted for attachment to the medication pen. A paper and foil "teardrop" label is heat sealed on the edge of the open end of the funnel shaped outer cover. In addition, the medication pen may have a cap received over the distal end of the medication pen, over the opening where the pen needle is installed. To install the pen needle on a medication pen, the user removes the medication pen cap. The user then removes the label on the pen needle outer cover and holds the outer cover to install the hub, typically threading the hub onto the pen. Once the hub is installed on the medication pen, the outer cover can be removed by pulling the outer cover distally off the hub. A separate inner needle shield sits over the needle, which the user must remove to administer an injection. The inner shield generally sits on the hub and simply helps the user locate the needle without forming a sterility barrier. After use, the user may use the outer cover to unthread the hub from the pen and dispose of the pen needle.

Medication pens and associated pen needles are disclosed in U.S. Pat. No. 7,645,264, and U.S. Patent Application Publication Nos. 2009/0069755 and 2012/0022460, all of which are incorporated by reference in their entirety for their teachings of pen needle design and construction. A device for arranging a releasable pen needle on an injection pen and releasing the pen needle into a mating storage or disposal container is disclosed in U.S. Pat. No. 8,057,444, also incorporated by reference for this teaching.

Pen needles can include a cover or shield to cover the end of the needle to prevent re-use and accidental needle stick. Pen needles are also known that have a shield to cover the proximal end of the needle when the pen needle is separated from the delivery device.

While the prior devices are generally suitable for the intended use, there is a need in the industry for improvements to the pen needles.

SUMMARY

The present disclosure is directed to a pen needle assembly for use with a medication delivery device for injecting a medication into a patient. The pen needle in one embodiment has a hub with a needle and a distal needle shield that can retract during use to expose the needle and extend to cover the distal end of the needle after use. In one embodiment, the needle shield can have a locking mechanism to lock the distal needle shield in the extended position and prevent re-use.

One feature of the pen needle is a retractable distal needle shield that can retract during use to expose the needle and slide to an extended position after use to cover the needle and provide a visual indicator to the user after use. A visual indicator can be positioned initially within the pen needle where the visual indictor is obscured from view. The indicator can connect to the distal needle shield when the needle shield slides to the retracted position. The indicator is carried with the distal needle shield when the needle shield moves to the extended position where the indicator is visible. In one embodiment, the indicator can be visible through a wall of the distal needle shield when indicator is coupled to the distal needle shield. In other embodiments, the indicator is visible through an opening in the hub when the distal needle shield is moved to an extended and locked position.

The pen needle is able to attach to a delivery pen or other delivery device where the pen needle includes a proximal needle shield that can lock in place after use to cover the non-patient end of the needle. The proximal needle shield for the non-patient end is in a retracted position before use and moves to an extended position after separation from the delivery device to cover the non-patient proximal end of the needle in the needle hub. A locking mechanism can be provided to lock the proximal needle shield for the non-patient end in the extended position to cover the proximal end of the needle or cannula and prevent re-use.

The pen needle in one embodiment includes a hub supporting a needle or cannula. A cover can be fitted over the end of the hub to cover the pen needle during storage until ready for use. A movable distal needle shield is coupled to the hub that can retract during use to expose the patient end of the needle and can be deployed by moving or sliding outwardly after use to cover the patient end of the needle and prevent further use or accidental needle stick. A biasing member, such as a spring member can be provided between the distal needle shield and the hub to bias the needle shield outwardly in a distal direction.

In one embodiment, a proximal needle shield is coupled to the pen needle for covering the non-patient proximal end of the needle when the pen needle is separated from the delivery device. A biasing member, such as a spring member, is provided within the hub for biasing the distal needle shield outwardly to the extended position covering the distal end of the needle and for biasing the second proximal needle shield outwardly to cover the proximal end of the needle. In one embodiment, a single spring member biases the distal needle shield and the proximal needle shield to the respective extended position.

In one embodiment, the pen needle includes a hub having a proximal end for attachment to a delivery device and a distal end, and a needle coupled to the hub and having a distal end extending from the distal end of the hub and proximal end at the proximal end of the hub. A distal needle shield is slidable in the hub between a first extended position to cover the distal end of the needle and a retracted position to expose the distal end of the needle and couple to an indicator provided in the hub. The distal needle shield is biased to a second extended position where the indicator separates from the hub and is visible to the operator when the distal needle shield is in the extended position.

In one embodiment, a pen needle has a hub with a needle having a distal end extending from the distal end of the hub and a proximal end at a proximal end of the hub. A distal needle shield is movable with respect to the hub between a first extended position to cover the needle and a retracted position to expose the needle. The distal needle shield is biased to a second extended position to lock the first needle shield in the second extended position to cover the distal end of the needle. A proximal needle shield is biased from a retracted position to an extended position to cover the proximal end of the needle when the pen needle is separated from the delivery device. A spring has a distal end engaging the distal needle shield to bias the distal needle shield to the extended position and a proximal end to bias the proximal needle shield to the extended position.

The first distal needle shield in one embodiment can include one or more flexible tabs that project radially outward and engage an inner surface of the hub. During use the first needle shield can rotate when retracted where the tabs slide into a groove or channel in the hub. The tabs slide into a recess in the channel thereby retaining the distal needle shield in a locked position.

The pen needle can include features of the invention can include a spring to actuate the first distal needle shield at the patient end to cover the distal end of the needle and the second proximal needle shield at the non-patient end to cover the proximal end of the needle after use.

The pen needle in one embodiment includes a hub having a proximal end for attachment to a delivery device and a distal end. A needle is coupled to the hub and has a distal end extending from the distal end of the hub. A distal needle shield is mounted in the hub for sliding between an extended position covering the distal end of the needle and a retracted position to expose the distal end of the needle. The distal needle shield is rotatable from a first angular position to a second angular position when the needled shield is retracted and slides outward in a linear direction after use to a locked position to cover the distal end of the needle. In one embodiment, the distal needle shield includes a detent that cooperates with a cam surface on the hub to rotate the distal needle shield by axial movement to the retracted position. Rotation of the distal needle shield aligns a tab on the distal needle shield with a guide channel in the hub.

The features of the pen needle include a hub having an internal cam member that rotates the first distal needle shield to align tabs on the first distal needle shield to a position where the tabs slide in a channel and lock the distal needle shield in the second extended position.

A method of using the pen needle, such as for injecting a substance into a patient, is also provided. The method retracts the needle shield from a first extended position to a retracted position to expose the needle and couple the needle shield to a visual indicator positioned in the hub. The needle shield then moves to a second extended position to cover the needle and couple the needle shield to a visual indicator positioned in the hub to lock the needle shield in the extended position.

A pen needle comprises a hub having a distal end, and a proximal end for attachment to a delivery device, a needle coupled to the hub and having a distal end extending from the distal end of said hub. A distal needle shield is coupled to the hub and slidable between a first extended position to cover the distal end of the needle and a retracted position to expose the distal end of the needle for injecting a substance into a patient, and a second extended position to cover the distal end of said needle. The distal needle shield is rotatable by axial movement relative to the hub from a first angular position in which the distal needle shield slides in said hub from the first extended position to the retracted position to a second angular position, and where the distal needle shield in the second angular position slides axially to the second extended position to a locked position.

In another embodiment, a pen needle comprises a hub having aside wall, a proximal end for attachment to a delivery device, and a distal end. A needle is coupled to said hub and has a distal end extending from the distal end of said hub and a proximal end at a proximal end of said hub. A distal needle shield is coupled to the hub for sliding in the hub between a first extended position to cover the distal end of the needle, a retracted position to expose the distal end of the needle, and a second extended position to cover the distal end of the needle, and wherein said distal needle shield is locked in the second extended position. A proximal needle shield is included at the proximal end of the hub and extends through an opening in the hub. The proximal needle shield is movable from a retracted position where the proximal end of the needle is exposed and an extended position where the proximal end of the needle is covered. Aa spring is included having a first end biasing the distal needle shield in a distal direction to the second extended position, and a second end biasing the proximal needle shield in a proximal direction to the extended position.

These and other aspects and features of the pen needle will be apparent from the following detailed description of the invention and the drawings.

BRIEF DESCRIPTION OF THE DRAWINGS

The following is a brief description of the drawings, in which.

Figure 1:
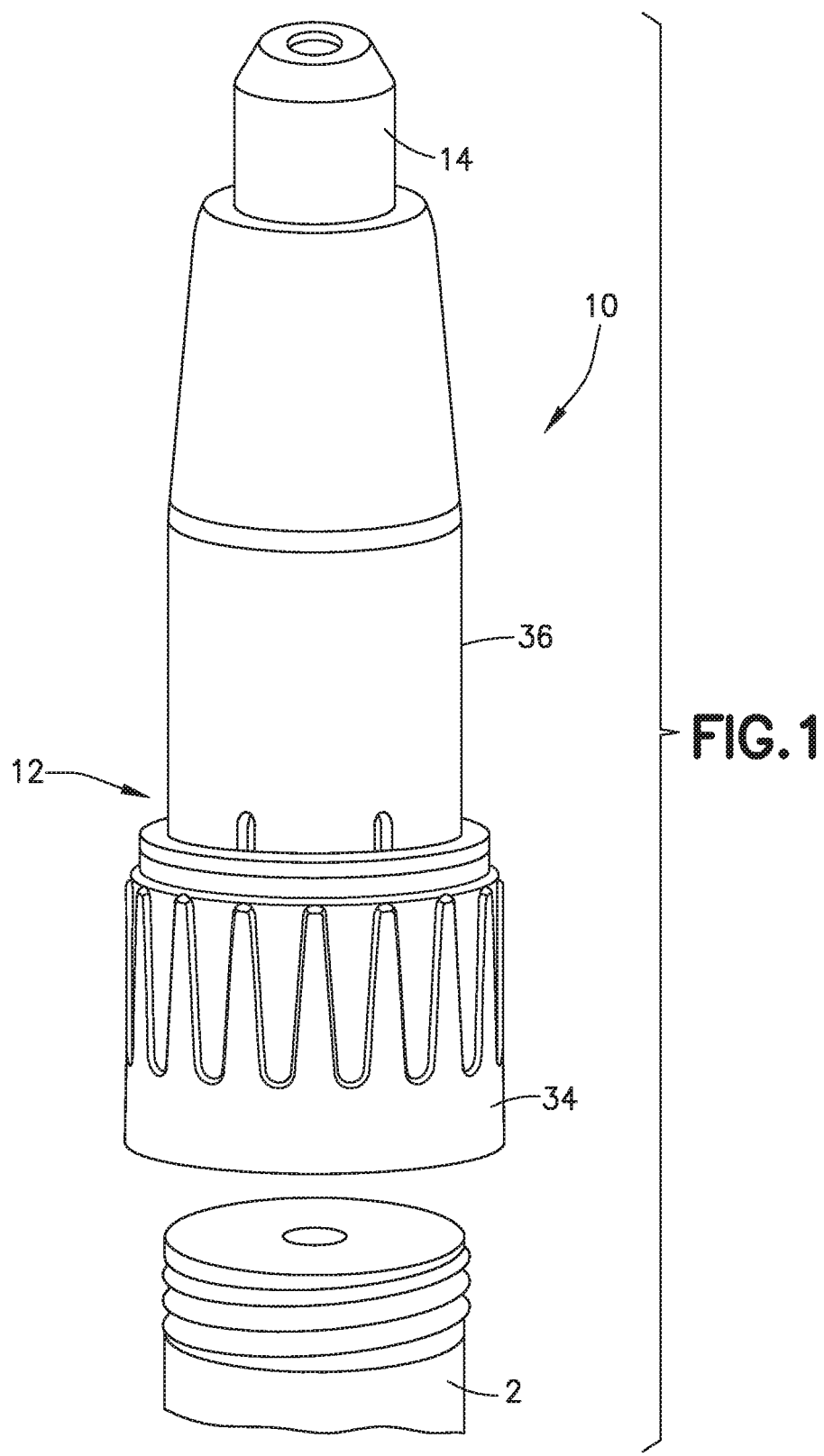
FIG. 1 is a side elevational view of the pen needle.

The figures are not to scale, and some features are omitted in certain views to better illustrate other features.

DETAILED DESCRIPTION

As used herein, the "distal" direction is in the direction of the injection site, and the "proximal direction" is the opposite direction. The "axial" direction is along the longitudinal axis of the injection device. The needle cannula is generally arranged axially in the device. "Radially" is a direction perpendicular to the axial direction. Thus, "radially inward" generally means closer to the needle. "Circumferentially" refers to arranging around the circumference, so that threads are arranged circumferentially on the end of a threaded fitting. The "top" view of a pen needle is looking at the pointed end of the needle. The different features of the embodiments can be used in combination with and used with other embodiments as long as the combined parts are not inconsistent with or interfere with the operation of the device and assembly.

A medication pen or delivery device is used herein to refer to a device having a medication compartment, typically containing multiple doses of medication, and a separate pen needle. The phrase "pen needle" refers to a needle-bearing assembly which can be attached to the medication pen body so that a proximal end of the pen needle assembly accesses a medication compartment and a distal end is adapted for insertion into an injection site to perform one or more injections. The terms "needle" and "cannula" are used herein interchangeably to refer to a thin tubular member having a sharpened end for insertion into an injection site on a subject. As used herein, the "distal" direction is in the direction toward the injection site, and the "proximal" direction is the opposite direction. "Axial" means along or parallel to the longitudinal axis of the needle and the "radial" direction is a direction perpendicular to the axial direction.

This disclosure is not limited in its application to the details of construction and the arrangement of components set forth in the following description or illustrated in the drawings. The embodiments herein are capable of being modified, practiced or carried out in various ways. The phraseology and terminology used herein is for the purpose of description and should not be regarded as limiting. The use of "including," "comprising," or "having" and variations thereof herein is to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not limited to physical or mechanical connections or couplings. Further, tens such as up, down, bottom, and top are relative, and are to aid illustration, but are not limiting. The embodiments are not intended to be mutually exclusive so that the features of one embodiment can be combined with other embodiments as long as they do not contradict each other. Terms of degree, such as "substantially", "about" and "approximately" are understood by those skilled in the art to refer to reasonable ranges around and including the given value and ranges outside the given value, for example, general tolerances associated with manufacturing, assembly, and use of the embodiments. The term "substantially" when referring to a structure or characteristic includes the characteristic that is mostly or entirely present in the structure.

Referring to the drawings, a pen needle 10 includes a needle hub 12. A cover can be included that fits over the pen needle 10 during storage and assists in attaching the pen needle 10 to a delivery device, such as a delivery pen 2 shown in FIG. 1. A closure or peel tab is generally provided over the open end of the cover to maintain the needle hub 12 is a sterile condition until ready for use. The delivery pen can be a standard delivery pen or other medication delivery device as known in the art for dispending and delivering a medication, such as insulin. An example of a suitable delivery pen is disclosed in U.S. Pat. No. 9,774,844 which is hereby incorporated by reference for this purpose.

In the embodiment shown in FIGS. 1-12, the pen needle 10 includes the hub 12, and a first distal needle shield 14 at a distal end of the hub 12. In one embodiment, a second proximal needle shield 16 is provided at a proximal end of the hub 12. The hub 12 is configured for supporting the distal needle shield 14 and the proximal needle shield 16. The hub can be a one piece unit or made from separate component that are coupled together. In the embodiment shown, the hub 12 includes a hub body 34 and a sleeve 36 connected by a suitable connection. The hub 12 includes an open bottom end 18 defining the proximal non-patient end 20 and a distal end 22 forming the patient end of the pen needle. The open bottom end 18 formed by the hub body has a side wall with internal threads 24 shown in FIG. 3 for coupling to the delivery pen in a known manner. The distal end 22 has an opening 26 for a needle 28 or cannula and defines the skin contact surface during use.

Needle 28 can be a hollow steel needle with a sharpened tip at a distal end at a proximal end and has a gauge and length for penetrating the skin to a desired depth and delivery of a medication to a patient. The needle 28 has patient end forming a distal end 30 with a sharpened tip extending from the distal end of the hub 12 for penetrating the skin of the patient. A proximal end 32 at the proximal end of the hub 12 is positioned for piercing a septum in the delivery device for receiving the drug or medication from the delivery device in a usual manner. The distal end 30 has an exposed length extending from the distal end of the hub during the injection of about 3-10 mm and typically about 4-6 mm.

Figure 2:
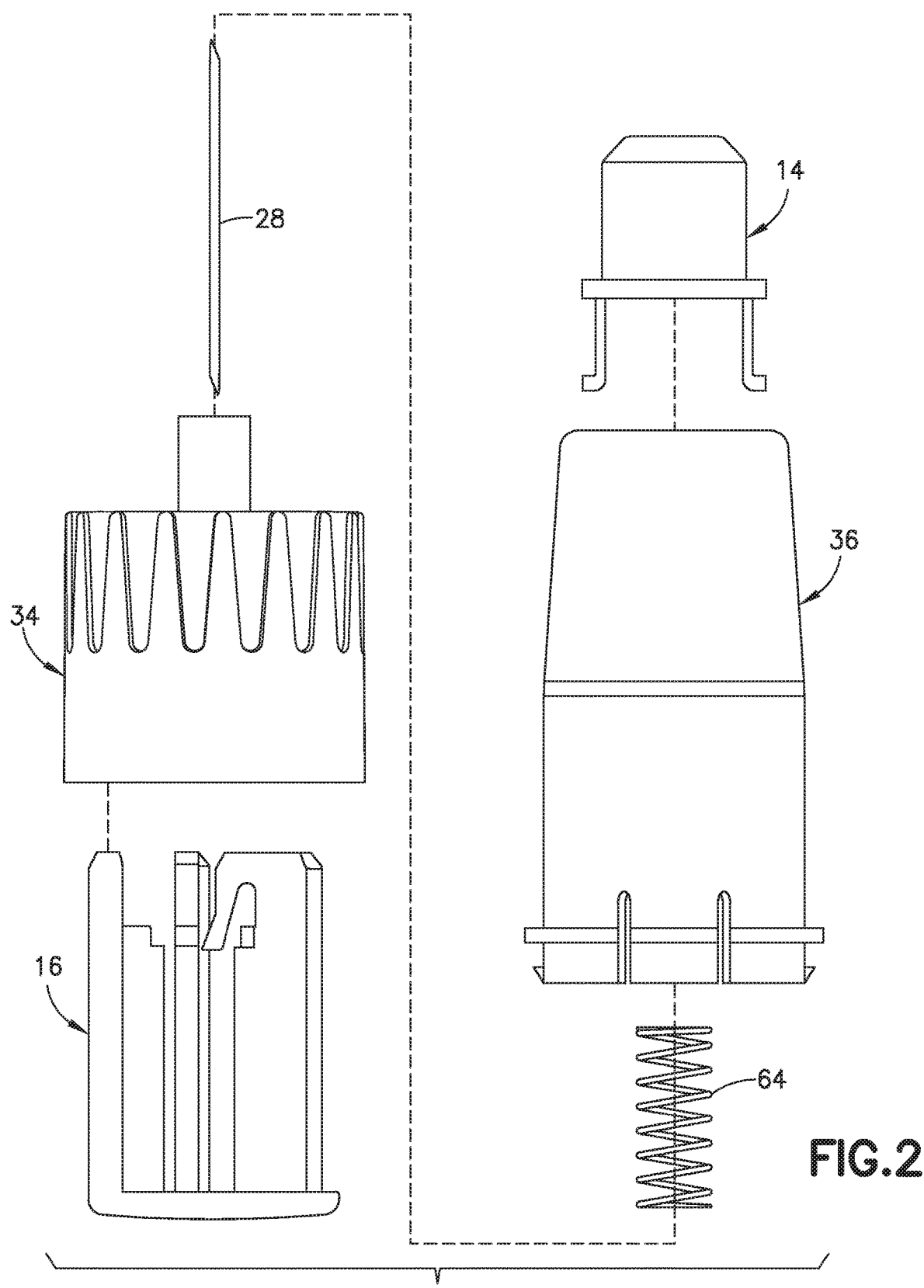
FIG. 2 is an exploded view of the pen needle of FIG. 1.
Figure 3:
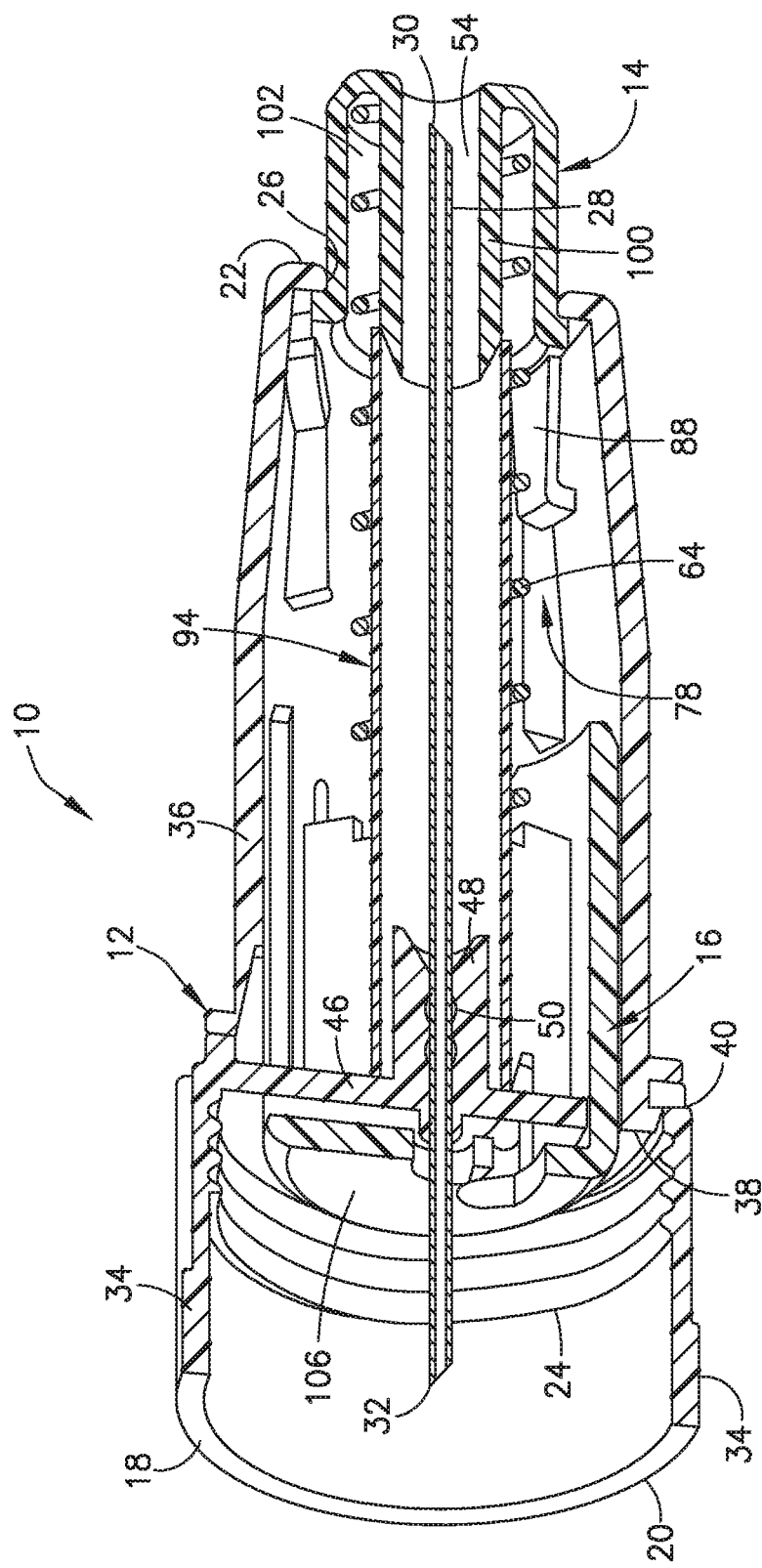
FIG. 3 is a perspective view of a pen needle in cross section showing the patent end first needle shield covering the needle and the non-patient end, second needle shield in a retracted position.

Referring to FIG. 3, the pen needle 10 includes the distal shield 14 and the proximal shield 16 for movement relative to the hub 12 and the needle 28. In the drawings, certain structural features and elements are not shown in each figure for clarity of the other elements. It is understood that the pen needle includes each of the elements as shown in FIGS. 1 and 2. The hub 12 can be a single member or can be formed as more than one member and coupled together by mechanical couplings, adhesives, welding and the like. In the embodiment shown in FIG. 1, the hub 12 has a hub body 34 with a side wall having a substantially cylindrical shape for coupling with the delivery device. As show, the threads 24 are formed on an inner surface of the side wall of the hub body 34. The hub 12 includes a housing shown as a sleeve 36 extending from the hub body 34 for receiving and supporting the components of the pen needle. The sleeve 36 in the embodiment shown has a proximal end 38 coupled to the top or distal end of the hub body 34 by tabs with hooks 40 although other method for coupling the sleeve 36 to the hub body 34 can be used. The sleeve 36 extends from the hub body 34 to form the distal end 22 of the hub 12. The opening 26 is formed in the end of the sleeve 36 to receive the first distal needle shield 14. The sleeve 36 has a length where the distal end 30 of the needle 28 extends from the distal end of the sleeve to define the exposed length of the needle during the injection.

Figure 4:
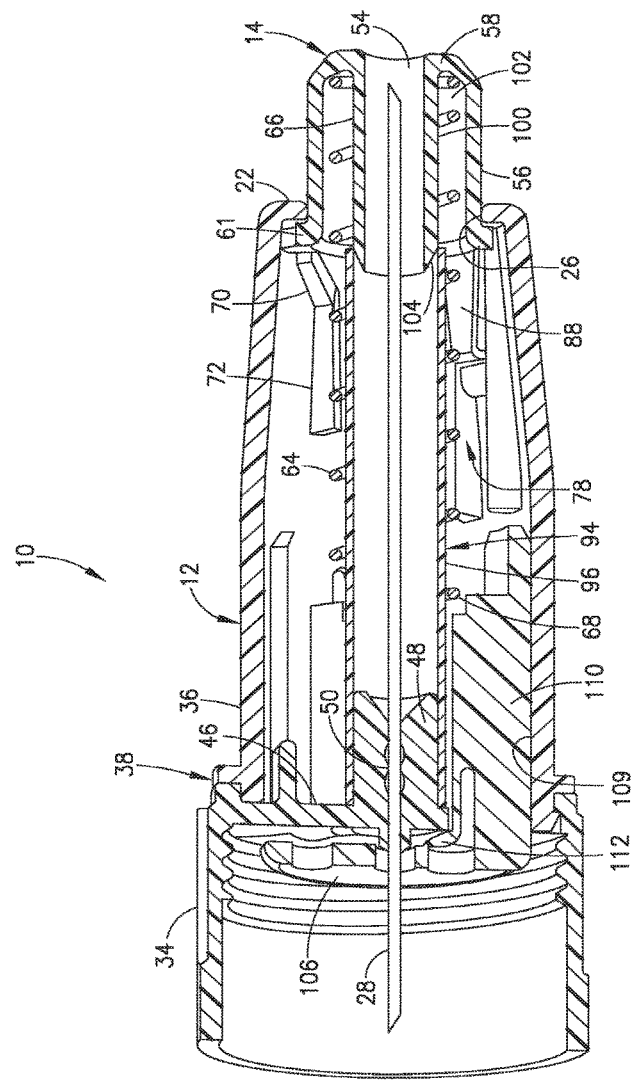
FIG. 4 is a cross sectional view of the pen needle showing the attachment mechanism of non-patient end needle shield.
Figure 5:
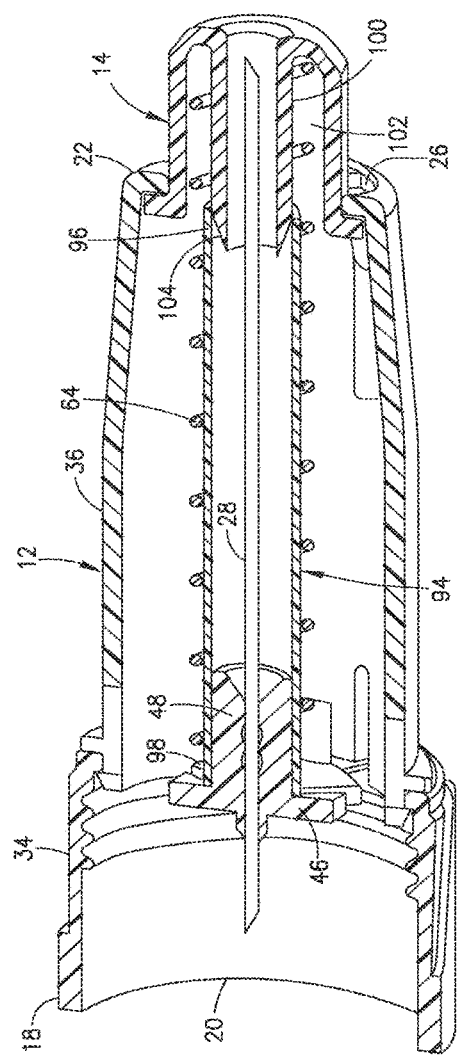
FIG. 5 is a cross sectional view of the pen needle showing the spring and indicator before actuating.
Figure 6:
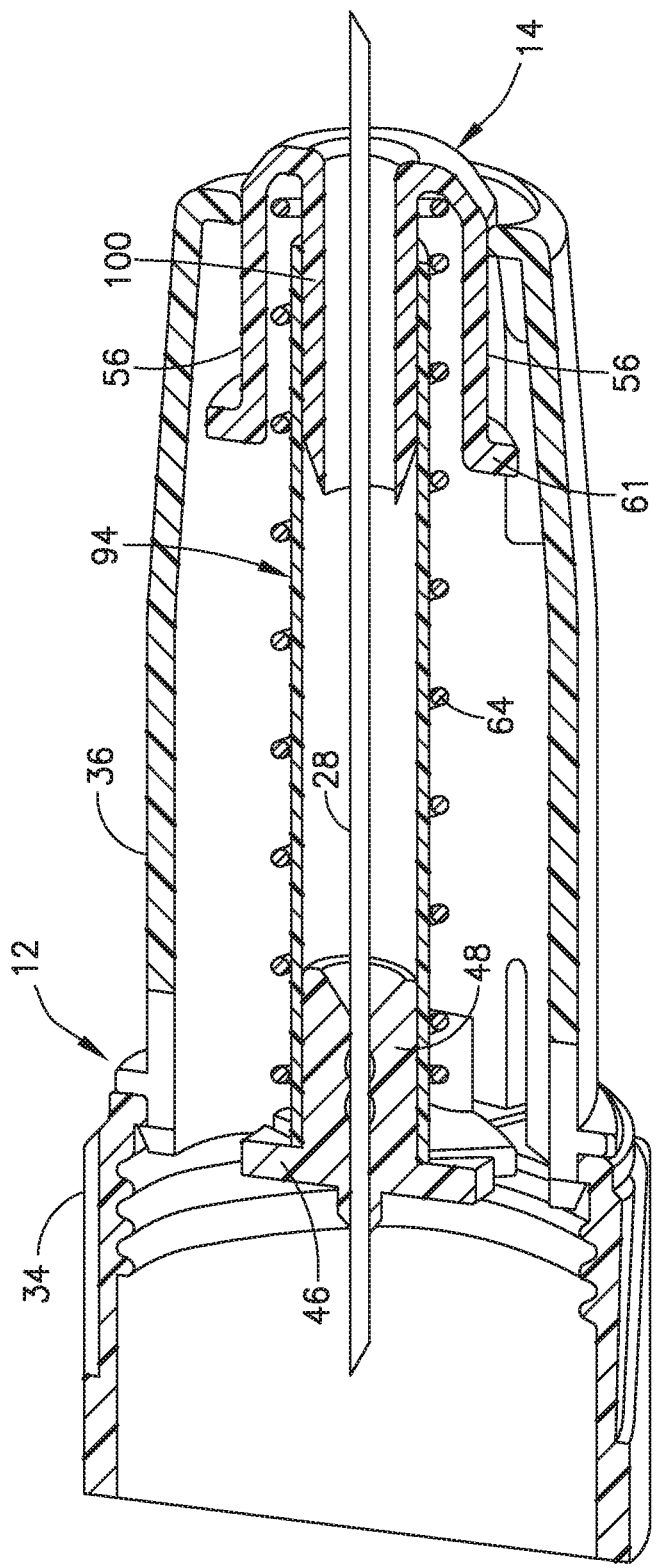
FIG. 6 is cross sectional view showing the indicator coupled to the shield.
Figure 7:
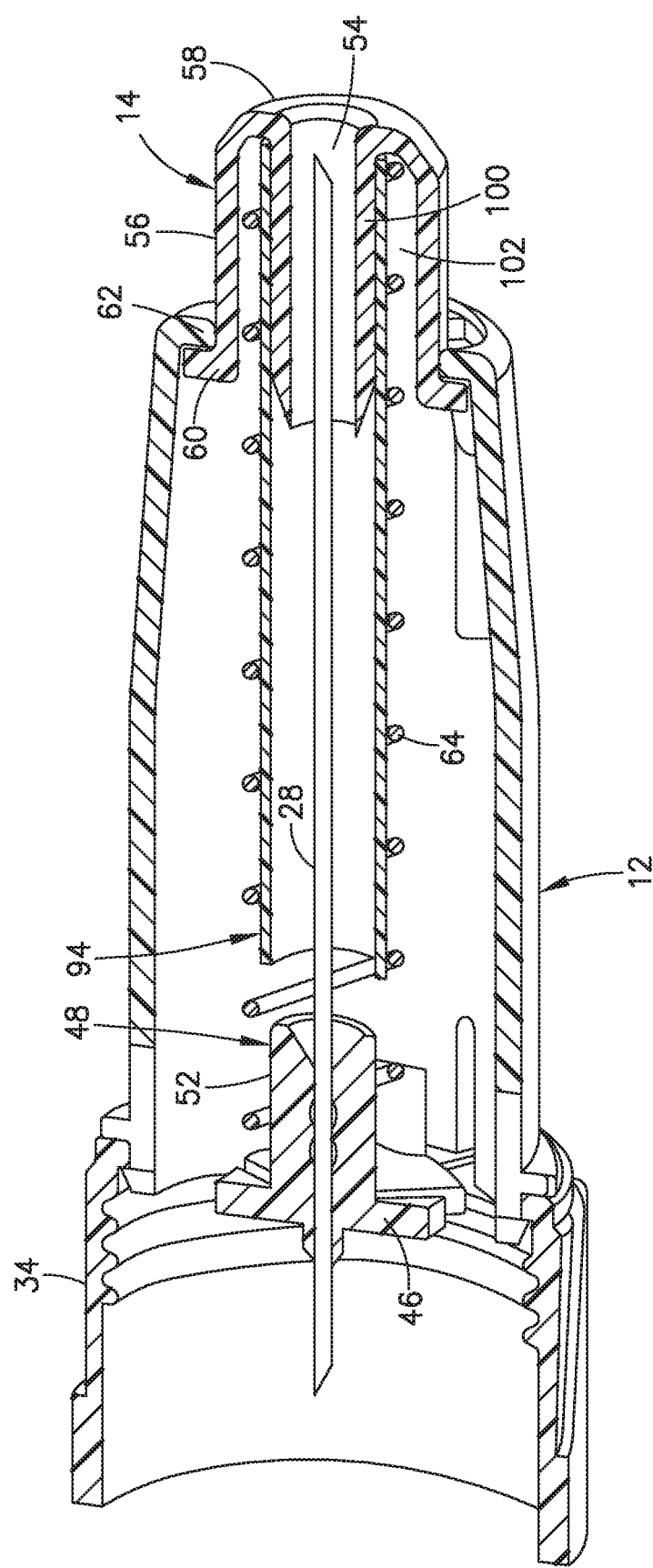
FIG. 7 is a cross sectional view showing the indicator coupled to the shield in the extended position.

Referring to FIGS. 2-4, the hub body 34 has an end wall 46 at the top distal end that can mate with the sleeve 36. The end wall 46 has a distal face with a post 48 extending in the distal direction. The post 48 has an axial passage 50 receiving and supporting the needle 28 as shown in FIG. 3. The needle 28 is fixed to the post 48 by an adhesive in a usual manner. In the embodiment shown, the post 48 has a substantially cylindrical configuration with a substantially cylindrical outer surface 52 as shown in FIG. 7. The distal end of the needle 28 projects from the post to extend distally from the pen needle a distance for penetrating the skin of the patient during an injection to a selected depth in the skin. The proximal end of the needle 28 extends within the hub body 34 a distance for connecting to a reservoir of the delivery device when the pen needle is attached to the delivery device.

The distal needle shield 14 forms a shield for the distal end 30 of the needle 28 to prevent re-use of the pen needle and prevent advertent needle stick before and after use. The distal needle shield 14 in the embodiment shown is configured for sliding within the open end of the hub 12 defined by the sleeve 36 between an extended position shown in FIG. 3 and a retracted position shown in FIG. 6. In the embodiment shown, the distal needle shield 14 has an axial passage 54 and an axial length to retract a distance to exposed the distal end 30 of the needle 28 for injecting the patient and to cover the distal end of the needle 28 when moved to the extended position shown in FIG. 7. The distal needle shield 14 has an outer wall 56 with a distal end 58 forming a skin contact surface. The distal needle shield has a proximal end with a coupling mechanism for coupling with the sleeve 36. In one embodiment, the coupling mechanism is an outwardly extending tab 60 for contacting the inwardly extending lip 62 at the open end of the sleeve 36. As shown in FIG. 7, a plurality of spaced apart tabs 60 are included for contacting the lip 62. The tabs 60 have a dimension for contacting the lip 62 to retain the distal needle shield 14 in the sleeve 36 when the distal needle shield 14 is in the extended position while allowing the needle shield 14 to slide between the retracted position and the extended position.

A biasing member is included for biasing the distal needle shield axially to the extended position. In the embodiment shown, the biasing member is a spring 64 positioned within the sleeve 36 of the hub 12 for biasing the needle shield 14 and the needle shield 16 outwardly in the axial direction to the respective extended positions. As shown in FIG. 3, the spring 64 is a first end 66 engaging the needle shield 14 and a second end 68 engaging the needle shield 16. The spring 64 is shown as a coil spring extending between the distal needle shield 14 and proximal shield 16 although other biasing members can be used for biasing needle shields to the extended position. In other embodiments, separate biasing members can be used to bias the distal needle shield and the proximal needle shield.

Figure 8:
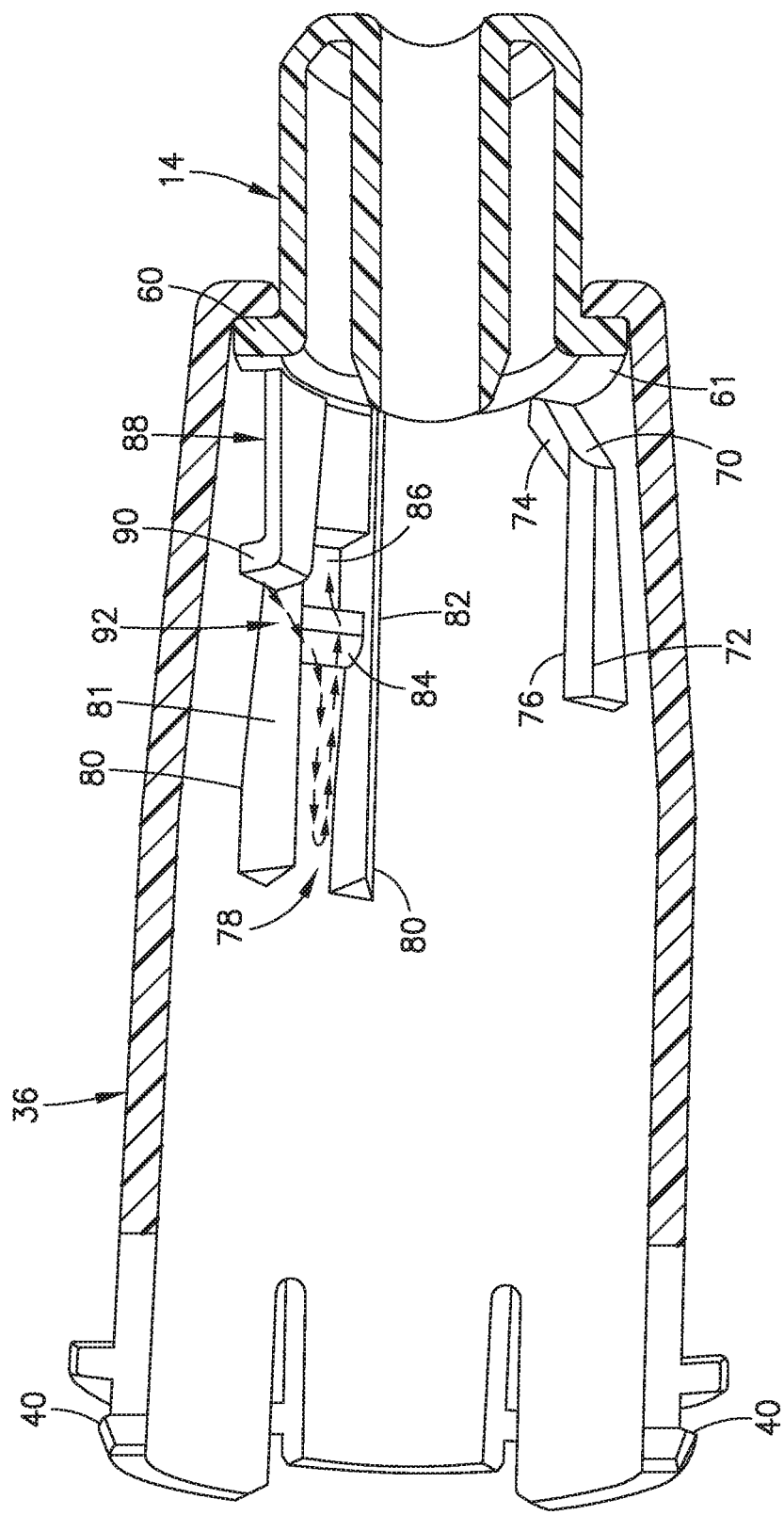
FIG. 8 is a cross sectional view of the sleeve showing the track for the needle shield.
Figure 9:
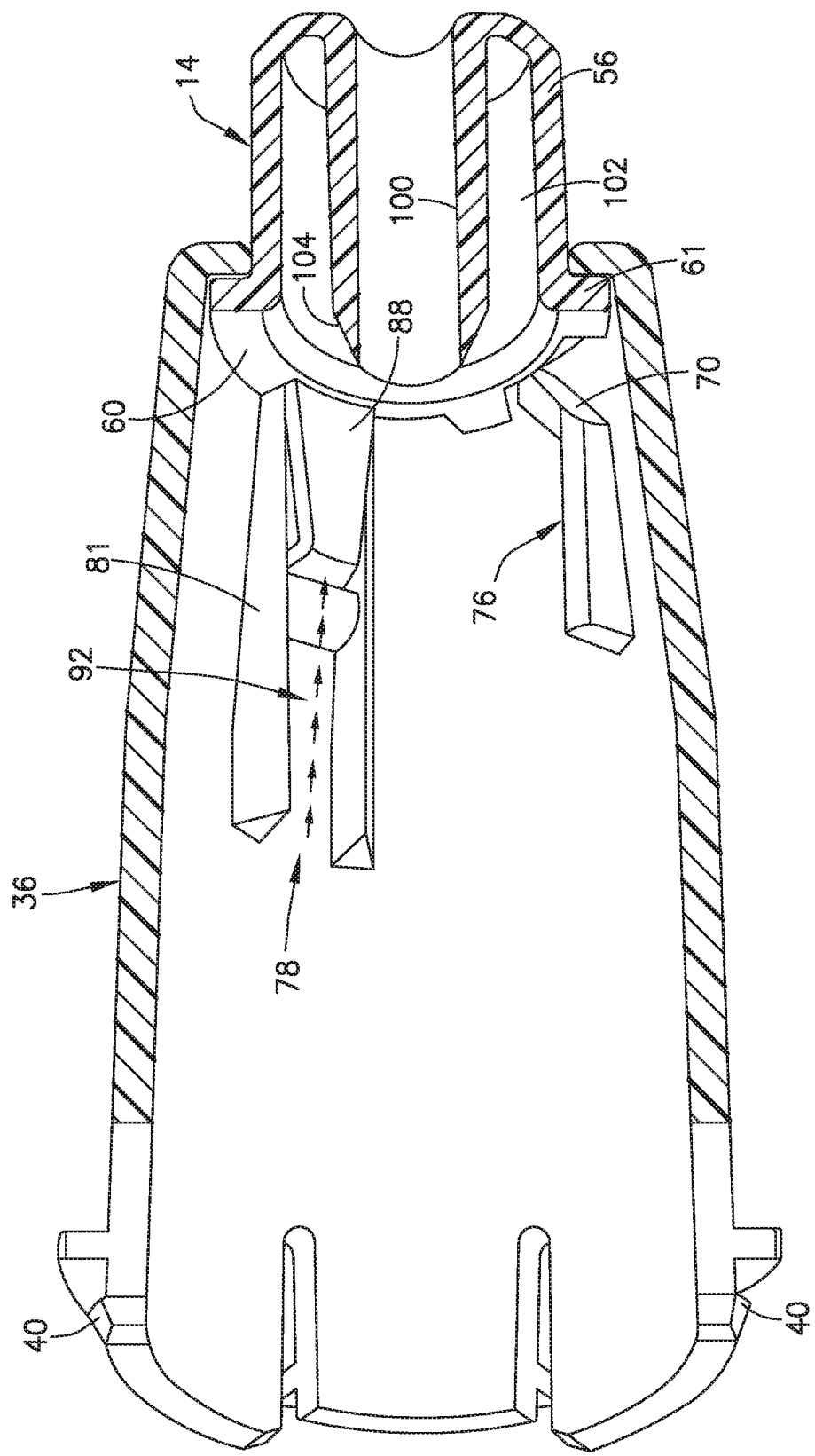
FIG. 9 is across sectional view showing the shield in the extended and locks position.

Referring to FIG. 8, the inner surface of the sleeve 36 can include an inclined cam surface 70 formed at an incline with respect to the longitudinal axis of the sleeve. The inclined cam surface 70 is formed by a protrusion 72 projecting radially inward from the inner surface of the sleeve. The cam surface 70 is formed on a first leg 74 of the protrusion 72. A second leg 76 extends in a substantially axial direction relative to the longitudinal axis of the sleeve 36. As shown in FIG. 8, a detent 91 on the needle shield 14 engages the cam surface 70 whereby moving the needle shield 14 axially inward causes the detent 91 to engage the inclined cam surface and rotate the needle shield 14 about the longitudinal axis of the pen needle.

Figure 10:
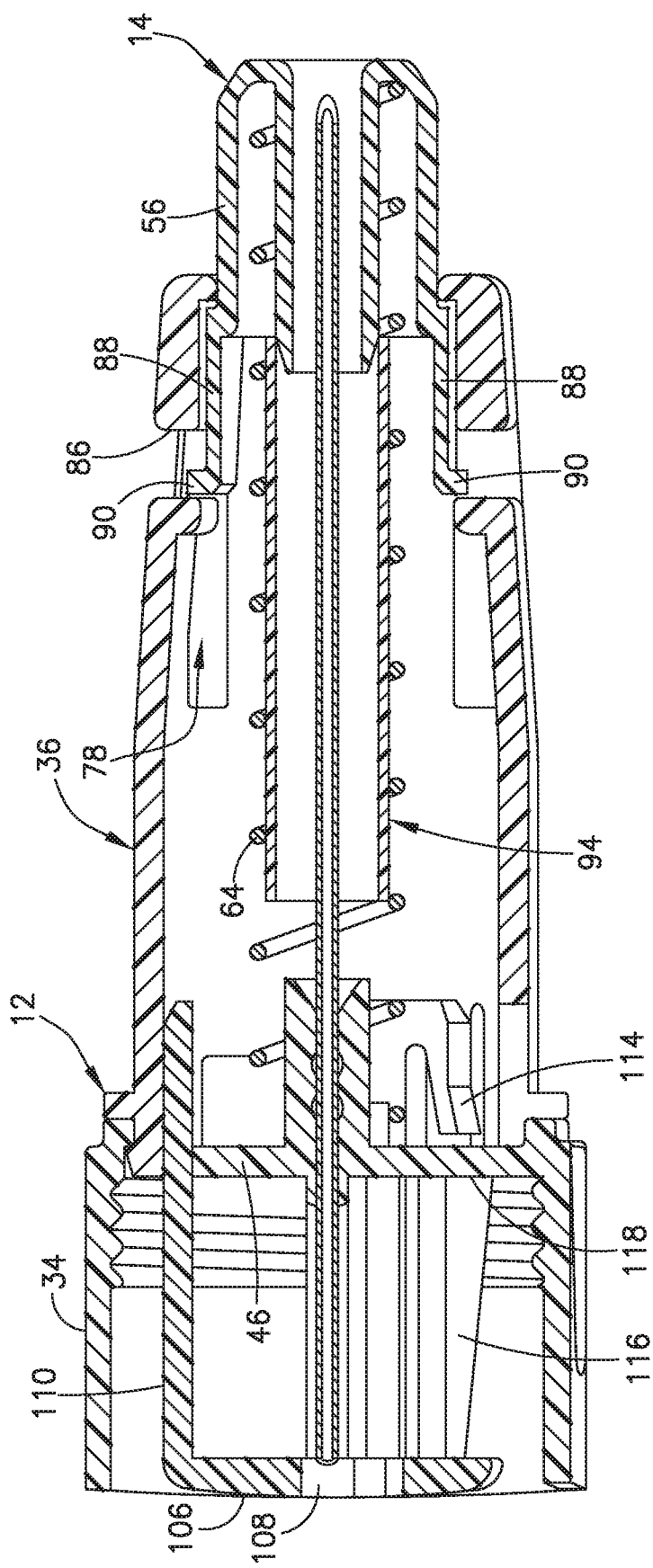
FIG. 10 is a cross sectional view of the first and second needle shields in the extended position.

As shown in FIG. 8 the inner surface of the sleeve 36 includes a guide channel 78 spaced circumferentially from the inclined cam surface 70. In the embodiment shown, a guide channels 78 is formed on opposite sides of the inner surface of the sleeve 36. The guide channel in the embodiment shown is formed between axially extending parallel ribs 80. A stop member 82 is formed in the guide channel 78 and is provided with an inclined surface 84 facing the proximal end of the hub 12. The stop member forms a recess 86 at the distal end portion of the guide channel 78. As shown in the embodiment of FIG. 10, the recess 86 can be an opening extending thought wall of the sleeve 36. In the embodiment shown, the guide channel 78 is formed by parallel ribs 80. In other embodiments, the channel 78 can be an axially extending recess formed on the inner surface of the sleeve where the opening in the side wall forms the stop member.

As shown in FIG. 8, the distal needle shield 14 includes a leg 88 forming a locking member for locking the needle shield 14 in a fixed position after use. The leg 88 extends axially from the proximal end of the distal needle shield 14. The leg 88 includes an outwardly extending tab 90. As shown in FIG. 8, the tab 90 is positioned on an outer surface of the axial rib 80 of the sleeve 36 in the initial position before use of the pen needle. During use, the needle shield 14 is pressed against the skin of the patient to retract the needle shield 14 while the needle 28 pierces the skin the patient. The needle shield 14 moves axially from the extended position shown in FIG. 3 to the retracted position shown in FIG. 6. As shown in FIG. 8, the detent 91 of the distal needle shield 14 engages the inclined cam surface 70 causing rotation of the distal needle shield 14 so that the tab 90 slides from the position shown in FIG. 8 into the guide channel 78 indicated by arrows 92 so that the tab 90 slides within the guide channel 78 to the retracted position shown in FIG. 6. The outer surface 81 of the rib 80 is formed at an incline to assist in guiding the tab 90 into the guide channel 78 by the rotational movement of the distal needle shield 14 relative to the hub. After the injection of the medication to the patient, the needle 28 is withdrawn from the patient whereby the distal needle shield 14 is biased to the extended position to cover the tip of the distal end of the needle 28. The tab 90 slides in the guide channel 78 and over the inclined surface 84 of the stop member 82 and into the recess 86. The stop member 82 has an inner face configured to contact the tab 90 and prevent the needle shield 14 from sliding to the retracted position after use of the pen needle. The tab 90 mates with the recess 86 to resist axial movement of the distal needle shield. In the embodiments where the recess in the guide channel 78 is an opening as in FIG. 10, the tabs 90 are visible through the opening providing a visual indicator to the user that the distal needle shield in the extended locked position. The tabs 90 can have a contrasting color relative to a color of the shield 36 to enhance the visualization of the tab in the locked position.

Referring to FIGS. 3-7, an indicator 94 can be positioned within the cavity of the hub 12 to provide a visual indication to the user or patient after use of the pen needle 10. The indicator 94 can be visualized through the distal needle shield when the distal needle shield is in the extended position. In the embodiment shown, the indicator 94 is a substantially cylindrical shaped sleeve 96 having an annular sidewall. In one embodiment, the sleeve 96 has a contrasting color with respect to the other components of the needle or other visual indicia. The indicator sleeve 96 has a proximal end 98 with an inner dimension complementing the outer dimension of the post 48. The indicator sleeve 96 fits on the post 48 by a friction fit to retain the sleeve 96 in position during manufacture and storage of the pen needle and to inhibit movement of the indicator sleeve until deployed. In the embodiment shown, the indicator 94 is surrounded by the spring 64.

Referring to FIGS. 3-7, in the embodiment shown, the distal needle shield 14 has an inner annular wall 100 defining the axial opening 54 of the needle shield 14. The annular wall 100 is spaced radially inward and concentric with the outer wall 56 of the needle shield 14. An annular recess 102 for receiving the spring 64 is formed between the outer wall 56 and the inner wall 100. The annular wall 100 has an outer surface with a dimension complementing the inner dimension of the indicator sleeve 96. The proximal end of the annular wall 100 has a chamfered surface or edge 104 for guiding the annular wall into the axial passage of the sleeve 96. The outer surface of the annular wall 100 has a dimension to form a friction fit with the inner surface of the sleeve 96 for coupling the sleeve to the annular wall. The outer surface of the annular wall 100 forms a gripping friction fit with the sleeve 96 having a gripping force greater than the gripping force between the sleeve 96 and the post 48 so that the sleeve 96 is retained on the annular wall 100 and separates the sleeve from the post 48 so that the indicator is carried by the distal needle shield when the distal needle shield slides to the extended position.

The distal needle shield 14 in the embodiment shown can be sufficiently transparent or translucent so that the indicator sleeve 96 is visible to the patient through the outer wall of the distal needle shield when the sleeve 96 is positioned within the annular recess 102 as shown in FIG. 10. The indicator sleeve 96 initially is oriented within the sleeve 36 of the hub body 12 and is not visible to the patient. Typically the sleeve 36 is opaque so that the indicator sleeve 96 is not visible. During use, the distal needle shield 14 is pressed against the skin of the patient to move the needle shield to the retracted position shown in FIG. 6 where the annular wall 100 slides into the axial passage of the indicator sleeve 96. The gripping force between the distal needle shield 14 and the indicator sleeve 96 enables separation of the sleeve 96 from the post 48 as the needle shield 14 is biased to the extended position shown in FIG. 7 where the tab 90 of the distal needle shield is captured by the recess 86 to lock the distal needle shield after use. The sleeve 96 positioned in the annular recess 102 is visible through the outer wall 56 of the needle shield 14 providing a visible indication to the patient or user that the pen needle has been used and the needle shield 14 is deployed to the locked position.

The proximal needle shield 16 is positioned in the hub body 34 and includes a base 106 oriented between the end wall 46 and the open proximal end 38. The base 106 has a central opening 108 for sliding around the proximal end of the needle 28. Legs 110 extend from the base 106 through the openings 109 in the end wall 46 of the hub body in a distal direction to engage the proximal end of the spring 46.

Figure 12:
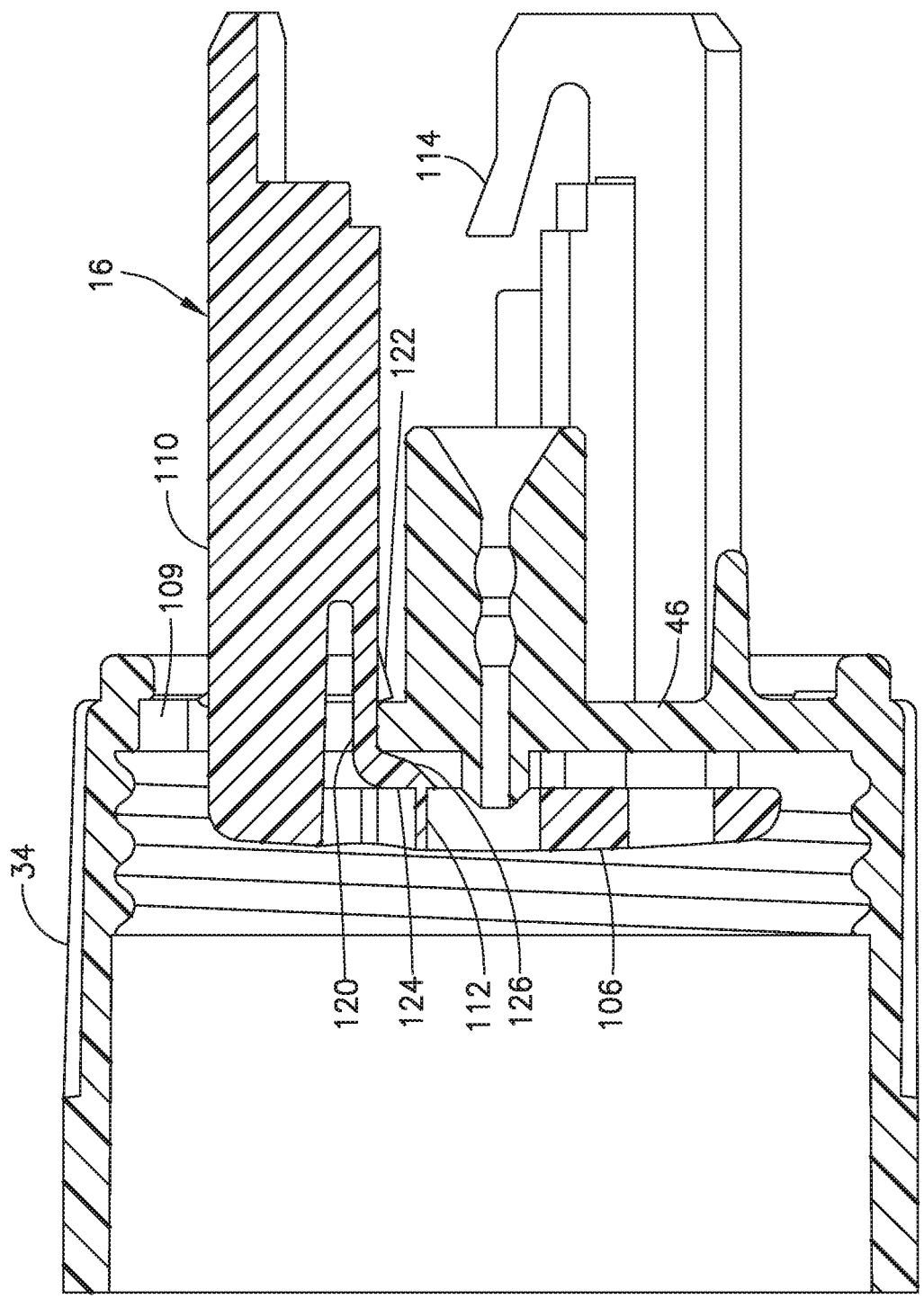
FIG. 12 is a cross sectional side view of the second needle shield showing the frangible member.

As shown in FIG. 12, the flexible arm 120 has an end connected to the leg 110 and extends toward the base 106. A detent forming a clip 122 projects inwardly from the arm 120 to engage a top surface of the end wall 46 of the hub body 34. The clip 122 contacts the end wall 46 to retain the needle shield 16 in the retracted position against the force of the spring 64. Referring to FIG. 12, a frangible member 112 extends between the base 106 and a flexible arm 120 to retain the base 106 and the proximal needle shield 16 in the retracted position against the biasing force of the spring as shown in FIG. 4 and FIG. 12. An outer distal end of the arm 120 has an inwardly extending tab 124 oriented on a bottom surface of the end wall 46. The end of the tab 124 is formed with a frangible member 112 as shown in FIG. 12. The distal face of the tab 124 forms an inclined cam surface 126 that engages the bottom surface of the end wall 46. The delivery device is connected to the hub body 34 so that the end of the delivery device engages the base 106 and forces the base 106 toward the end wall 46. The movement of the base 106 forces the cam surface 126 into contact with the edge of the opening 109 in the end wall 46 forcing the arm 120 outwardly and separating the clip 122 from the end wall 46 and breaking the frangible member 112. The arm 120 is biased radially outward so that breaking the frangible member 112 spring the arm 120 radially outward to separate the clip 122 from the end wall 46 allowing the proximal needle shield to move to the extended position. When the delivery device separates from the hub body 34, the spring biases the needle shield 16 to the extended position shown in FIG. 7.

Figure 11:
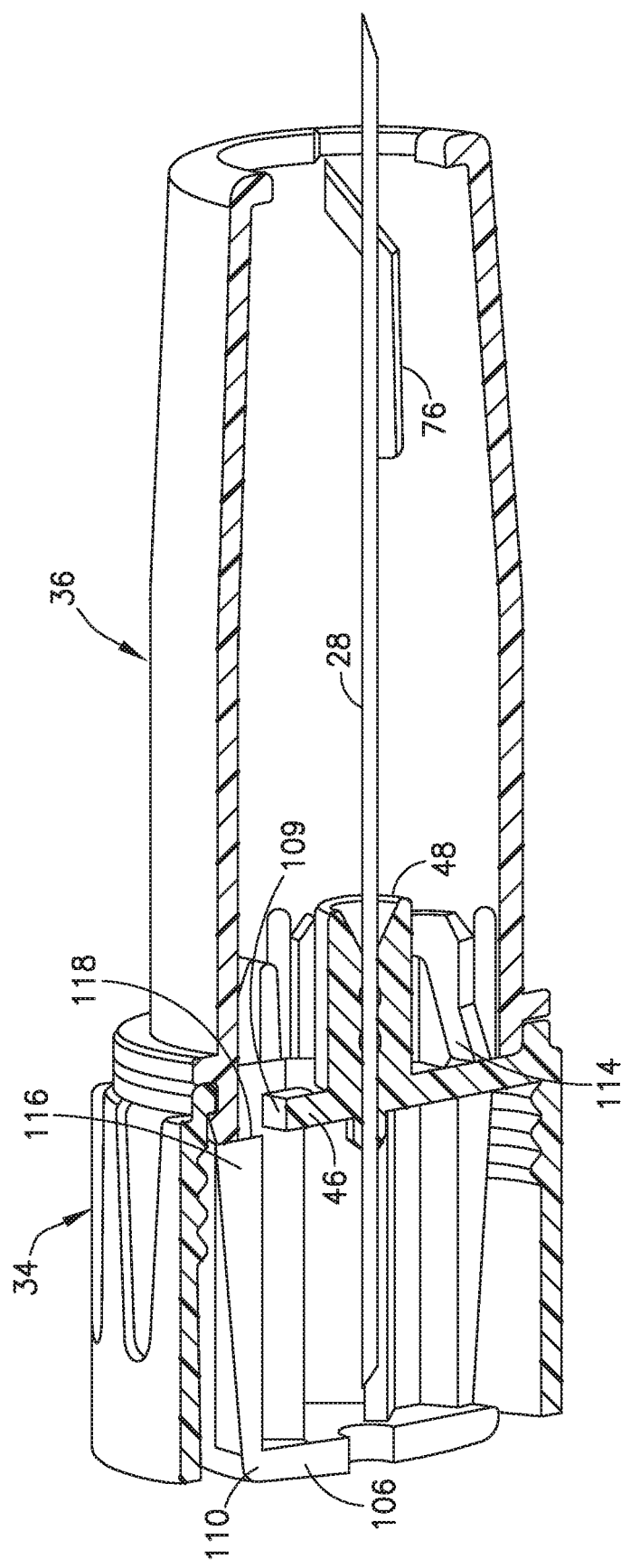
FIG. 11 is a cross sectional view showing the needle shield of non-patient end of the pen needle.

The legs 110 have a distal end with a stop member 114 for engaging the distal face of the wall of the hub body when the proximal needle shield 16 is deployed thereby limiting the distance the needle shield 16 travels when deployed. Flexible ribs 116 extend radially outward from the legs 110. The base 106 of the proximal needle shield 16 is initially spaced from the wall of the hub body as shown in FIG. 4. The hub body is attached to the delivery device by the threaded connection 24 so that the base 106 engages the end of the delivery device. Threading the hub body onto the delivery device compresses the base 106 toward the wall 46 of the hub body to break the frangible member 112. After injecting the patient with the medication from the delivery device, the hub body is separated from the delivery device. The spring 64 biases the proximal needle shield toward the proximal end of the hub body to slide the base 106 over the proximal end of the needle as shown in FIG. 8. The stop member 114 engages the top face of the end wall 46 of the hub body to prevent further sliding movement of the needle shield to the extended position. The flexible ribs 116 slide through the opening 109 in the end wall 46 and are biased outwardly to spring outwardly when the flexible ribs clear the end wall of the hub body. The flexible ribs 116 have a distal face 118 that spring outwardly to engage the bottom surface of the end wall of the hub body when the proximal needle shield is in the extended position to prevent retraction of the shield 16 after use as shown in FIG. 11.

In the embodiments, the components of the hub and shield are typically injection molded plastic, such as acrylonitrile butadiene styrene (ABS), polyethylene, polypropylene, or the like. The needle can be a surgical grade stainless steel. Other materials and methods of manufacture known to those of ordinary skill in the art of medication pen technology may be adapted for use herein without departing from the scope of the invention. To assemble the parts, the hub assembly may be constructed with the needle separately, with adhesive applied in the interface area to secure the cannula to the hub, and this sub-assembly may then be assembled with the other components.

The foregoing description of the preferred embodiments is not to be deemed limiting of the invention, which is defined by the following claims. The foregoing description should provide the artisan of ordinary skill with sufficient information to practice variants of the embodiments described. Features and improvements described in dependent claims or in connection with one embodiment may be combined with those of another independent claim or another embodiment, provided they are not inconsistent therewith, without departing from the scope of the invention.

The invention claimed is:

1. A pen needle, comprising:
    a hub having a distal end, and a proximal end for attachment to a delivery device;
    a needle coupled to said hub and having a distal end extending from said distal end of said hub;
    a distal needle shield coupled to said hub and slidable between a first extended position to cover said distal end of said needle, a retracted position to expose said distal end of said needle for injecting a substance into a patient, and a second extended position to cover said distal end of said needle, wherein said distal needle shield is rotatable by axial movement relative to said hub from a first angular position in which said distal needle shield slides in said hub from said first extended position to said retracted position to a second angular position, and where said distal needle shield in the second angular position is configured to slide axially to the second extended position, which is a locked position; and
    an indicator positioned in said hub, where said distal needle shield is configured to couple to said indicator when moved to the retracted position, and said indicator is carried by said distal needle shield when said distal needle shield is moved to the second extended position, where said indicator is visible when said distal needle shield moves to the second extended position, wherein:
        said distal needle shield is configured to couple to said indicator by a first friction fit when moved to the retracted position; and
        said indicator is coupled to said hub by a second friction fit by a first gripping force, and said distal needle shield is coupled to said indicator by the first friction fit having a second gripping force greater than said first gripping force, whereby said indicator is configured to be coupled to said distal needle shield and separated from said hub by movement of said distal needle shield to the second extended position.

2. The pen needle of claim 1, wherein said indicator is received within said distal needle shield and is visible through a wall of said distal needle shield.

3. The pen needle of claim 1, wherein said distal needle shield has a transparent wall, where said indicator is visible through said transparent wall when said indicator is coupled to said distal needle shield.

4. The pen needle of claim 3, wherein said indicator has an axial passage, and said distal needle shield includes an inner wall configured for engaging an inner surface of said axial passage of said indicator for the coupling of said indicator to said distal needle shield.

5. The pen needle of claim 1, wherein said distal needle shield has an outer wall with an outwardly extending tab for mating with a recess on an inner surface of said hub to lock said distal needle shield in the second extended position.

6. The pen needle of claim 5, wherein said inner surface of said hub has a guide channel for receiving said outwardly extending tab on said distal needle shield, and said recess is located in said guide channel oriented to receive said outwardly extending tab of said outer wall and lock said distal needle shield in the second extended position.

7. The pen needle of claim 6, wherein said inner surface of said hub has a cam surface for engaging a detent on said distal needle shield, said cam surface spaced circumferentially from said guide channel and oriented to rotate said distal needle shield to said second angular position where said outwardly extending tab engages said guide channel and said recess.

8. The pen needle of claim 7, wherein said outwardly extending tab on said distal needle shield is spaced from said guide channel when said distal needle shield is in said first extended position, and where said outwardly extending tab is received in said guide channel when said distal needle shield is in the retracted position and in the second extended position.

9. The pen needle of claim 6, wherein said inner surface of said hub has spaced apart axially extending ribs forming said guide channel between said axially extending ribs.

10. The pen needle of claim 6, where said recess in said hub is an opening extending through a wall of said hub, and where said outwardly extending tab on said distal needle shield is visible when said outwardly extending tab is received in said opening indicating said distal needle shield is in the locked position.

11. The pen needle of claim 6, wherein said outwardly extending tab on said distal needle shield is visible through said hub when said outwardly extending tab is received in said recess indicating said distal needle shield is in the locked position.

12. The pen needle of claim 1, further comprising a proximal needle shield configured for covering a proximal end of said needle, and where said proximal needle shield is connected to a frangible member to retain said proximal needle shield in a retracted position, and where said frangible member is configured to break to enable said proximal needle shield to move to an extended position to cover said proximal end of said needle.

13. The pen needle of claim 12, wherein said proximal needle shield further comprises a flexible rib to engage said hub to lock said proximal needle shield in the extended position.

14. The pen needle of claim 12, further comprising a spring having a first end engaging said distal needle shield for biasing said distal needle shield to the second extended position, and a second end engaging said proximal needle shield for biasing said proximal needle shield to the extended position.

15. The pen needle of claim 14, wherein said hub has an inner wall with an opening and where said proximal needle shield extends through said opening in said inner wall, said proximal needle shield having a distal end on a first side of said inner wall for engaging the spring, and a second end on a second side of said inner wall for covering said proximal end of said needle.

16. The pen needle of claim 14, wherein said spring comprises a coil spring, and where said spring has an axial passage, said first end engaging said distal needle shield and said second end engaging said proximal needle shield.

17. The pen needle of claim 16, wherein the indicator is positioned in said axial passage of said coil spring.

18. The pen needle of claim 1, wherein said indicator is received within said distal needle shield and is visible through a wall of said distal needle shield.

19. A pen needle, comprising:
    a hub having a distal end, and a proximal end for attachment to a delivery device;
    a needle coupled to said hub and having a distal end extending from said distal end of said hub;

a distal needle shield coupled to said hub and slidable between a first extended position to cover said distal end of said needle, a retracted position to expose said distal end of said needle for injecting a substance into a patient, and a second extended position to cover said distal end of said needle, wherein said distal needle shield is rotatable by axial movement relative to said hub from a first angular position in which said distal needle shield slides in said hub from said first extended position to said retracted position to a second angular position, and where said distal needle shield in the second angular position is configured to slide axially to the second extended position, which is a locked position;

an indicator positioned in said hub, where said distal needle shield is configured to couple to said indicator when moved to the retracted position, and said indicator is configured to be carried by said distal needle shield when said distal needle shield is moved to the second extended position, where said indicator is visible when said distal needle shield moves to the second extended position;

a proximal needle shield configured for covering a proximal end of said needle, and where said proximal needle shield is connected to a frangible member to retain said proximal needle shield in a retracted position, and where said frangible member is configured to break to enable said proximal needle shield to move to an extended position to cover said proximal end of said needle; and a spring having a first end engaging said distal needle shield for biasing said distal needle shield to the second extended position, and a second end engaging said proximal needle shield for biasing said proximal needle shield to the extended position, wherein:

said spring comprises a coil spring, and where said spring has an axial passage, the first end engaging said distal needle shield and the second end engaging said proximal needle shield; and the indicator is positioned in said axial passage of said coil spring.

20. A pen needle, comprising:

a hub having a distal end, and a proximal end for attachment to a delivery device;

a needle coupled to said hub and having a distal end extending from said distal end of said hub;

a distal needle shield coupled to said hub and slidable between a first extended position to cover said distal end of said needle, a retracted position to expose said distal end of said needle for injecting a substance into a patient, and a second extended position to cover said distal end of said needle, wherein said distal needle shield is rotatable by axial movement relative to said hub from a first angular position in which said distal needle shield slides in said hub from said first extended position to said retracted position to a second angular position, and where said distal needle shield in the second angular position is configured to slide axially to the second extended position, which is a locked position; and an indicator positioned in said hub, where said distal needle shield is configured to couple to said indicator when moved to the retracted position, and said indicator is configured to be carried by said distal needle shield when said distal needle shield is moved to the second extended position, where said indicator is visible when said distal needle shield moves to the second extended position, wherein said indicator is received within said distal needle shield and is visible through a wall of said distal needle shield.

* * * * *